US012617781B2

(12) United States Patent
Tang et al.

(10) Patent No.: US 12,617,781 B2
(45) Date of Patent: May 5, 2026

(54) UTIDELONE SEMI-HYDRATED SINGLE CRYSTAL AND PREPARATION METHOD THEREFOR AND USE THEREOF

(71) Applicants: Beijing Biostar Pharmaceuticals Co., Ltd., Beijing (CN); Chengdu Biostar Pharmaceuticals, LTD., Chengdu (CN)

(72) Inventors: Li Tang, Beijing (CN); Rixiang Kong, Beijing (CN); Rongguo Qiu, Beijing (CN)

(73) Assignees: Beijing Biostar Pharmaceuticals Co., Ltd., Beijing (CN); Chengdu Biostar Pharmaceuticals, Ltd., Chengdu (CN)

( * ) Notice: Subject to any disclaimer, the term of this patent is extended or adjusted under 35 U.S.C. 154(b) by 986 days.

(21) Appl. No.: 17/757,979

(22) PCT Filed: Apr. 8, 2021

(86) PCT No.: PCT/CN2021/085903
§ 371 (c)(1),
(2) Date: Jun. 24, 2022

(87) PCT Pub. No.: WO2021/204188
PCT Pub. Date: Oct. 14, 2021

(65) Prior Publication Data

US 2023/0041956 A1 Feb. 9, 2023

(30) Foreign Application Priority Data

Apr. 8, 2020 (CN) ......................... 202010282801.7

(51) Int. Cl.
*C07D 417/06* (2006.01)

(52) U.S. Cl.
CPC ........ *C07D 417/06* (2013.01); *C07B 2200/13* (2013.01)

(58) Field of Classification Search
CPC .......................... C07D 417/06; C07B 2200/13
See application file for complete search history.

(56) References Cited

U.S. PATENT DOCUMENTS

2019/0070152 A1* 3/2019 Tang .................... A61K 31/427

FOREIGN PATENT DOCUMENTS

| | | | |
|---|---|---|---|
| CN | 1521258 | A | 8/2004 |
| CN | 101519404 | A | 9/2009 |
| CN | 102101863 | A | 6/2011 |
| CN | 107041886 | A | 8/2017 |
| JP | 2003528090 | A | 9/2003 |
| JP | 2011513248 | A | 4/2011 |
| JP | 2013514281 | A | 4/2013 |
| JP | 2019504893 | A | 2/2019 |
| WO | 0170716 | A1 | 9/2001 |
| WO | 02060904 | A2 | 8/2002 |

OTHER PUBLICATIONS

International Search Report issued on Jul. 8, 2021 for International Patent Application No. PCT/CN2021/085903 (6 pages).
Kazuhide Ashizawa, "Optimization and Crystallization Technology of Salt/Crystal Form," Pharm Tech Japan (2002); 18 (10), pp. 81-96.
Noriyuki Takada, "Cocrystal Screening and Its Application in Improvement of Pharmaceutical Properties of APIs," Pharm Tech Japan (2009); 25(12): pp. 155-166.
Hirayama, N., "Drug Crystallization Method," Handbook for Crystallization Preparation of Organic Compounds, Maruzen Co., Ltd. (2008): pp. 57-84.
Noriyuki Takada, "API Form Screening and Selection in Drug Discovery Stage," Pharm Stage (2007); 6(10): pp. 20-25.
Handbook of Pharmaceutics, Nanzando Co., Ltd. (1989); 1: pp. 28, 76, and 80.
Kazuhide Ashizawa, "Polymorphism and Crystallization of Pharmaceuticals," Polymorphism and Crystallization Science of Drugs, Maruzen Yukisei Co., Ltd. (2002): pp. 273, 278, and 305-317.
1st Japanese Office Action issued on Jun. 13, 2023 for Japanese Patent Application No. 2022-538911 (3 pages).

* cited by examiner

*Primary Examiner* — Sarah Pihonak
*Assistant Examiner* — Mikhail O'Donnel Robinson
(74) *Attorney, Agent, or Firm* — Fox Rothschild LLP

(57) ABSTRACT

A polycrystal form of Utidelone, particularly relating to a semi-hydrated crystal form (A) of Utidelone, a preparation method therefor and a use of crystal Utidelone in preparation of a pharmaceutical composition, especially the use in preparation of a pharmaceutical composition for inhibiting tumor growth and treating solid tumors of mammals, especially human. The provided crystal form is stable and resistant to high temperature and high humidity, and the preparation method is diversified and simple, and is suitable for industrialized production of new medicines.

8 Claims, 4 Drawing Sheets

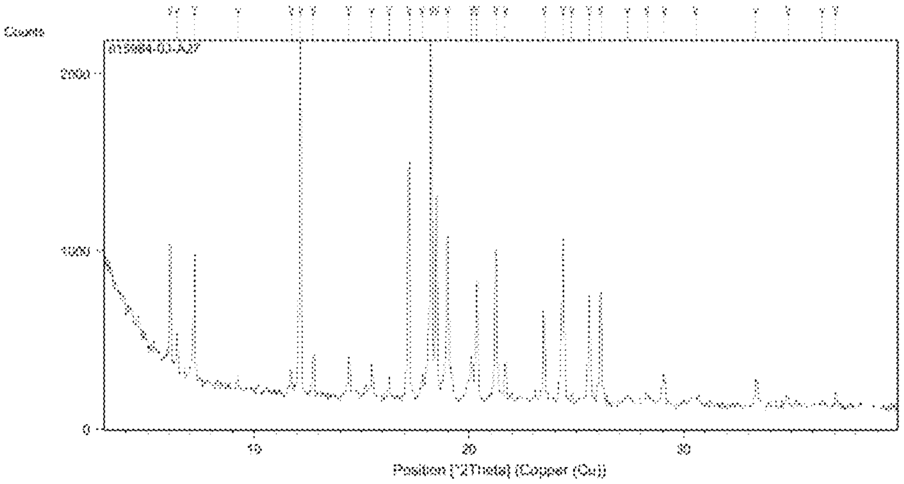
FIG. 1 X powder diffraction pattern of Utidelone semihydrate crystal
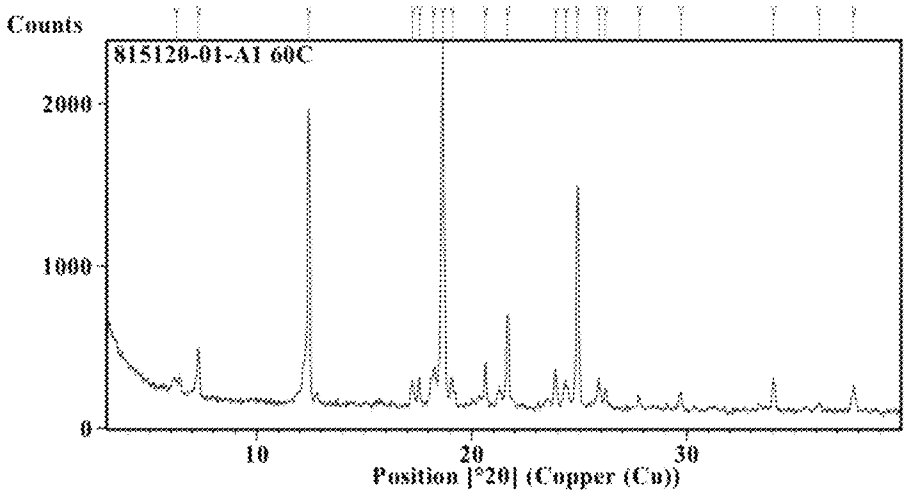
FIG. 2 X powder diffraction pattern of Utidelone anhydrate crystal

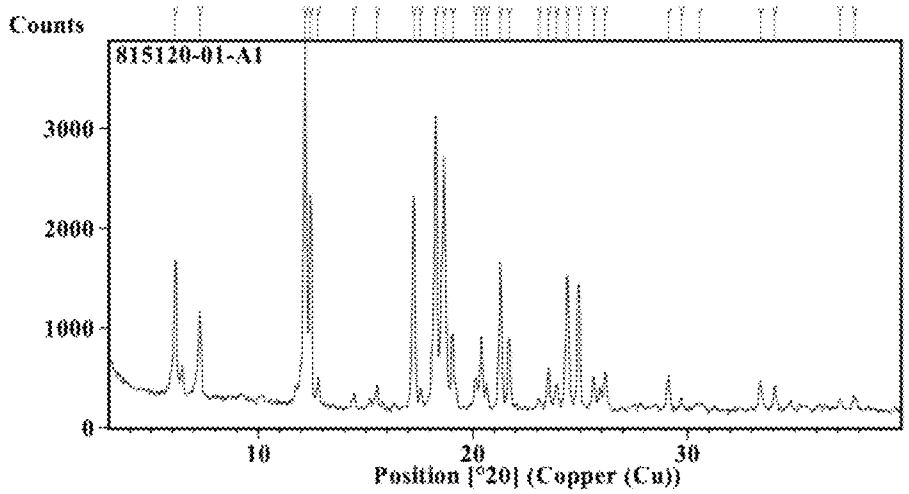
FIG. 3 X powder diffraction pattern of mixed crystals of Utidelone
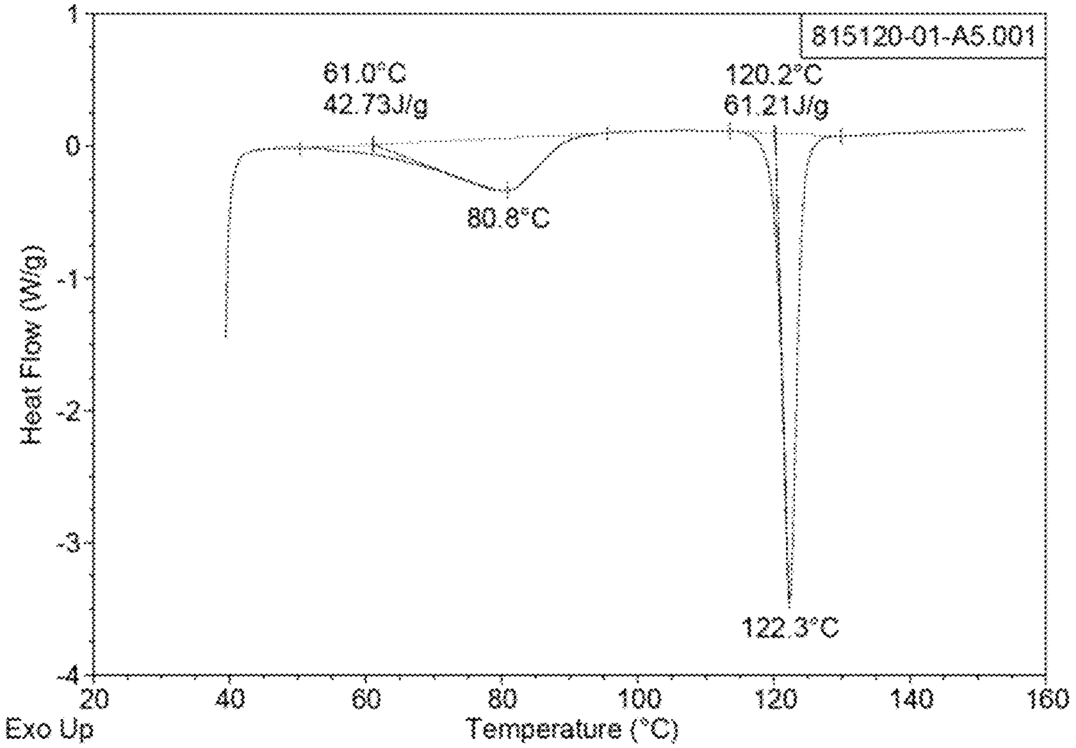
FIG. 4 DSC pattern of Utidelone semihydrate crystal

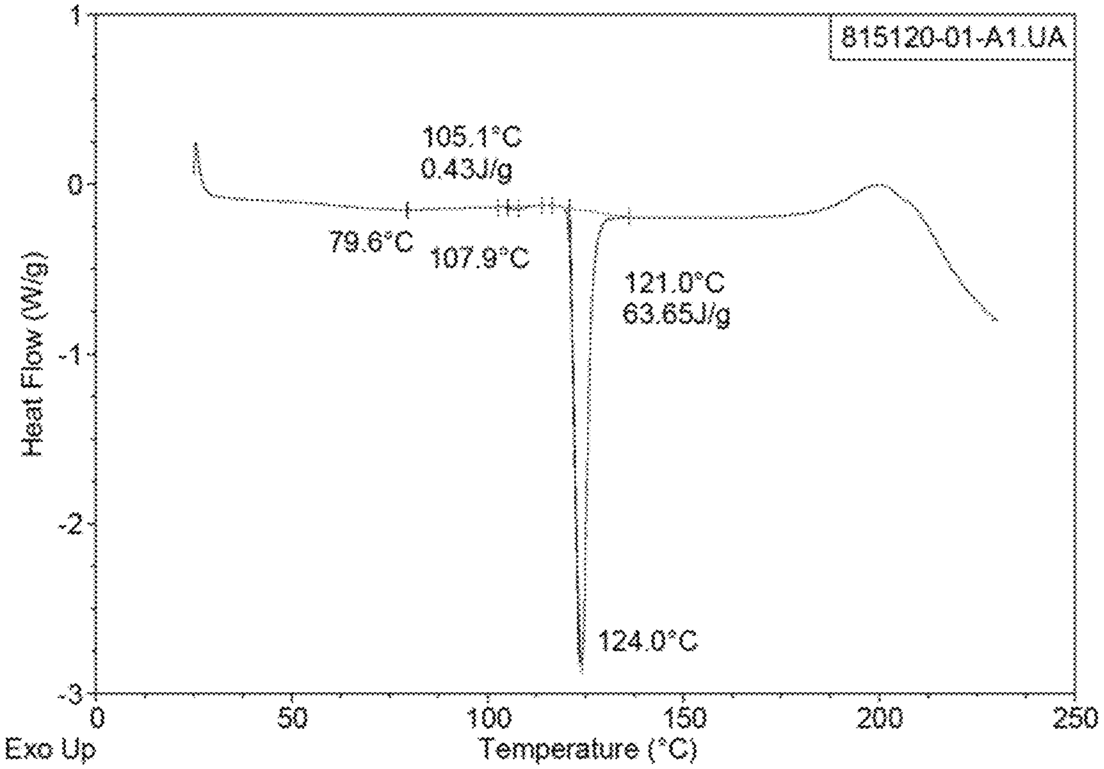
FIG. 5 DSC pattern of Utidelone anhydrate crystal
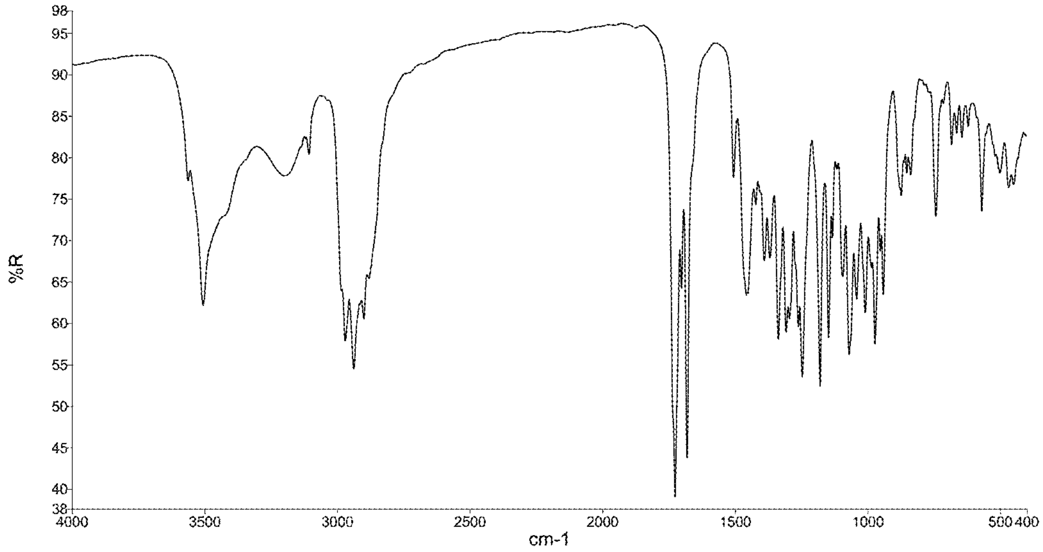
FIG. 6 IR absorption spectrum of Utidelone semihydrate crystal

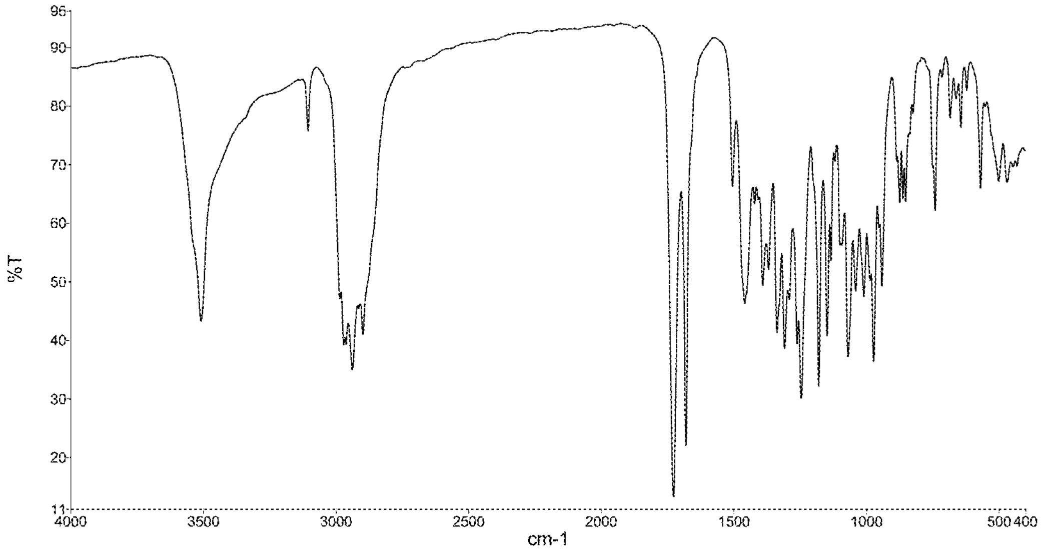
FIG. 7 IR absorption spectrum of Utidelone anhydrate crystal
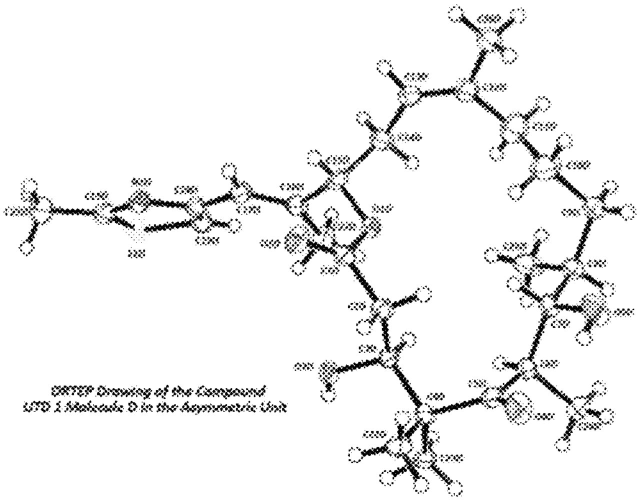
FIG. 8 Single crystal diffraction pattern of Utidelone compound

UTIDELONE SEMI-HYDRATED SINGLE CRYSTAL AND PREPARATION METHOD THEREFOR AND USE THEREOF

CROSS REFERENCE TO RELATED APPLICATIONS

This application is the U.S. national phase of International Patent Application No. PCT/CN2021/085903, filed on Apr. 8, 2021, which claims priority to Chinese Patent Application No. 202010282801.7, filed on Apr. 8, 2020, the disclosures of which are incorporated herein by reference in their entirety.

TECHNICAL FIELD

The present invention relates to 4S, 7R, 8S, 9S, 13Z, 16S-4,8-dihydroxy-5,5,7,9,13-pentamethyl-16-[E-1-methyl-2-(2-methyl)-1,3-thiazol-4-yl)-prop-1-en-2-yl]-hexadecoxetan-13-en-2,6-one lactone (i.e. Utidelone) semi-hydrate crystal and its preparation method and use for preparing a pharmaceutical composition, especially use for preparing an antitumor drug.

BACKGROUND ART

Utidelone is an epothilone compound. Epothilone is a class of 16-membered macrolide natural cytotoxic compounds produced by the metabolism of microbial *Myxobacteria*. It has a similar mechanism of action to paclitaxel and has obvious antitumor activity. They both induce the polymerization of tubulin to form a hyperstable state, inhibit microtubule depolymerization, hinder mitosis, prevent tumor cell reproduction, and thus lead to apoptosis. Epothilone shows strong antitumor activity in p-glycoprotein expressing multidrug-resistant tumor cell lines, and has better water solubility than paclitaxel. Epothilone is superior to paclitaxel in many aspects and is considered to be a updated product of paclitaxel.

As a member of epothilone family, Utidelone is chemically named 4S, 7R, 8S, 9S, 13Z, 16S-4,8-dihydroxy-5,5,7,9,13-pentamethyl-16-[E-1-methyl-2-(2-methyl)-1,3-thiazol-4-yl)-prop-1-en-2-yl]-hexadecoxetan-13-en-2,6-one lactone with the following structural formula:

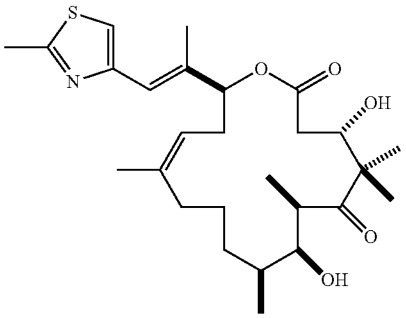

Utidelone may be used to treat solid tumors including breast cancer, lung cancer, colon cancer, gastrointestinal tumors such as stomach cancer, gynecological tumors such as ovarian cancer and cervical cancer, head and neck squamous cell carcinoma, esophageal cancer, pancreatic cancer, bile duct cancer, skin cancer, brain cancer and liver cancer. Different crystal forms of a API may have significant differences in hygroscopicity, stability, and bioavailability, which may affect the efficacy of the drug. It is crucial to find a suitable crystal form for the development of a pharmaceutical composition of Utidelone. So far, no related crystal forms of Utidelone have been reported.

SUMMARY

In one aspect, the present invention provides a crystal form of Utidelone with extremely high stability. The present invention provides a single crystal of Utidelone, which is Utidelone semihydrate crystal (crystal form A). The X-ray diffraction pattern is shown in FIG. 1, the DSC is shown in FIG. 6, and the single crystal diffraction pattern is shown in FIG. 8.

In another aspect, the present invention provides a method for preparing Utidelone semihydrate crystal. The preparation method includes dissolving Utidelone in a solvent, standing or stirring at 2-25° C., and then crystallizing. The solvent is a mixture of n-heptane and tetrahydrofuran or a mixture of dichloromethane and n-heptane. Single crystal with high purity may be obtained from the mixed solvent.

In an embodiment, the preparation method is described as follows: weigh 3.0 mg of Utidelone compound as an initial sample into a 3 mL glass bottle, add 0.2 mL of the mixed solvent listed in Table 1 below, swirl and sonicate appropriately, complete dissolution of the solid sample was then observed. Subsequently, the above-mentioned 3 mL glass bottle was capped and sealed, and allowed to stand at room temperature. After 5 days, white needle-like solids or flaky crystal were precipitated. According to XRPD detection, the crystal form of the compound prepared by this preparation method is Utidelone semihydrate crystal, that is, a crystal form of Utidelone semihydrate in which 4 Utidelone molecules and 2 water molecules are contained. The X-ray powder diffraction pattern of the crystal form A is basically the same as that in FIG. 1. Through the X-ray diffraction analysis, the Utidelone semihydrate crystal of the present invention is a single flaky crystal, and single crystal X-ray diffraction pattern shows that the crystal belongs to triclinic system, P1 space group, and its unit cell parameters are: {a=6.37029(4)Å, b=14.67305(10)Å, c=29.54548(12)Å, α=81.3294(4°), β=86.3641(4°), γ=86.6019(5°), V=2721.14 (3)Å3} □ and Z value is 4. The experimental details relating to the crystal structure, analysis of the results, and the refinement parameters for Utidelone semihydrate crystal are listed in Table 2.

The crystal structure is an asymmetric structural unit, and the asymmetric structural unit of the crystal is composed of four Utidelone molecules (crystallographically independent) and two water molecules, which indicates that the crystal is the semihydrate of Utidelone compound.

The single crystal data have successfully confirmed the stereochemical structure of Utidelone. The absolute configuration of the chiral centers in the molecule is {C3(S), C6(R), C7(S), C8(S), C16 (S).

The DSC (Differential Scanning Calorimetry) analysis of the Utidelone crystal shows that the semihydrate has two characteristic signals in DSC. The first one with a relatively broad endothermic signal between 50-110° C. is due to dehydration of Utidelone semihydrate to form the anhydrous form. The second one with relatively sharp endothermic peak at 122±3° C. is due to the melting of the substance (FIG. 4). However, Utidelone anhydrate crystal has only one characteristic signal in DSC, which is a relatively sharp endothermic peak at 122±3° C. due to the melting of the substance (FIG. 5).

The Utidelone crystal of the present invention is characterized by infrared (IR) spectroscopy. Measurements were performed using 10-20 mg of Utidelone semihydrate in 300 mg of potassium bromide. According to the IR spectral characterization in FIG. 6, the crystal form of Utidelone semihydrate has absorption bands at wavenumber IR (KBr) νmax 3506, 2968, 2938, 2901, 1726, 1680, 1456, 1246, 971 cm-1.

The Utidelone semihydrate crystal provided by the present invention has good stability at high temperature and high humidity, and is beneficial to maintain its specific physical properties under storage and production conditions.

Utidelone crystal has stronger stability at high humidity than Utidelone powder. Under high humidity conditions, the semihydrate crystal is very stable, and the water content does not change significantly. Utidelone crystal also has stronger stability at high temperature. It may be stored at 60° C. for more than 1 year, and stored at 40° C. for more than 3 years without changes in substance, i.e., it is stable for long-term storage at high temperature.

Crystal A is determined to be the most stable crystal, which is stable for a long time under normal storage conditions and is chemically stable.

In another aspect, the present invention provides a use of the crystal form of Utidelone in preparing a pharmaceutical composition.

Based on the antitumor effects of Utidelone, another aspect of the present invention relates to a use of Utidelone to prepare a pharmaceutical composition containing Utidelone semihydrate crystal for treating diseases. The pharmaceutical composition includes a parenteral injection and an oral formulation such as a capsule or a tablet, containing 10-50 mg of the compound in polymorphic form. The therapeutically effective amount of the pharmaceutical composition of the present invention or the polymorphic form of Utidelone is provided herein for treating preferably cancers in mammals, especially humans.

DESCRIPTION OF DRAWINGS

FIG. 1 is the X powder diffraction pattern of Utidelone semihydrate crystal;

FIG. 2 is the X powder diffraction pattern of Utidelone anhydrate crystal;

FIG. 3 is the X powder diffraction pattern of mixed crystals of Utidelone;

FIG. 4 is the DSC pattern of Utidelone semihydrate crystal;

FIG. 5 is the DSC pattern of Utidelone anhydrate crystal;

FIG. 6 is the IR absorption spectrum of Utidelone semihydrate crystal;

FIG. 7 is the IR absorption spectrum of Utidelone anhydrate crystal;

FIG. 8 is single crystal diffraction pattern of Utidelone compound.

EMBODIMENTS

EXAMPLES

The following examples are intended to further illustrate Utidelone crystal of the present invention and its preparation method in detail, and the content of the present invention is not limited to these examples.

Example 1

Place 100 mg of Utidelone in a 100 ml glass bottle, add 6 ml of a mixed solvent of tetrahydrofuran/n-heptane (1:5, v/v), swirl, sonicate, and mix evenly, and observe till solids were completely dissolved. The glass bottle was then sealed with a cap and placed at room temperature. After 5 days, long flaky single crystals were observed. The crystals were collected and filtered through vacuum filtration. After filtration, the crystals were washed with 30-35% ethanol solution, and then dried in a drying oven to a moisture content of 1.8-3%. According to the X-ray diffraction pattern (FIG. 1), the resulting crystal is a 0.5 semihydrate crystal (A), which is a single crystal lattice. The single crystal diffraction pattern of Utidelone is shown in FIG. 8.

TABLE 2

Experimental data and structural refinement parameters for the crystal structure analysis of Utidelone semihydrate

| | |
|---|---|
| Identification code | 815984-03-A27 |
| Empirical formula | $C_{27}H_{41}NO_5S$•0.5 $H_2O$ |
| Formula weight | 500.67 |
| Temperature | 120.00(10) K |
| Wavelength | Cuκα (λ = 1.54184 Å) |
| Crystal system, space group | Triclinic, P1 |
| Unit cell dimensions | a = 6.37029(4) Å<br>b = 14.67305(10) Å<br>c = 29.54548(12) Å<br>α = 81.3294(4)°<br>β = 86.3641(4)°<br>γ = 86.6019(5)° |
| Volume | 2721.14(3) $Å^3$ |
| Z, CalMolated density | 4, 1.222 $g/cm^3$ |
| Absorption coefficient | 1.363 $mm^{-1}$ |
| F(000) | 1084.0 |
| Crystal size | 0.22 × 0.0214 × 0.014 $mm^3$ |
| 2 Theta range for data collection | 6.062 to 133.184 |
| Limiting indices | −7 ≤ h ≤ 7<br>−17 ≤ k ≤ 17<br>−35 ≤ l ≤ 35 |
| Reflections collected/ Independent reflections | 115262/18890 [$R_{int}$ = 0.0534, $R_{sigma}$ = 0.0322] |
| Refinement method | Full-matrix least-squares on $F^2$ |
| Completeness | 98.0% |
| Data/restraints/parameters | 18890/3/1319 |
| Goodness-of-fit on $F^2$ | 1.057 |
| Final R indices [ I ≥ 2sigma(I)] | $R_1$ = 0.0394, $wR_2$ = 0.1022 |
| Final R indices [all data] | $R_1$ = 0.0419, $wR_2$ = 0.1063 |
| Largest diff. peak and hole | 0.61/−0.28 e · $Å^{-3}$ |
| Flack parameter | −0.002(7) |
| Bayesian statistics on Bijvoet differences[1] | Hooft y = −0.003(6), P2(true) = 1.000, P3(true) = 1.000, P3(rac-twin) = 0.0E+00, P3(false) = 0.0E+00, corr. coeff = 0.993 |

TABLE 3

X-ray powder diffraction results of Utidelone semihydrate

| Pos. [°2Th.] | Height [cts] | FWHM Left [°2Th.] | d-spacing [Å] | Rel. Int. [%] |
|---|---|---|---|---|
| 6.078971 | 651.907200 | 0.076752 | 14.53936 | 32.71 |
| 6.389271 | 176.976100 | 0.076752 | 13.83392 | 8.88 |
| 7.207470 | 690.563800 | 0.076752 | 12.26521 | 34.65 |
| 9.222558 | 63.109330 | 0.076752 | 9.58935 | 3.17 |
| 11.693990 | 138.175400 | 0.076752 | 7.56768 | 6.93 |
| 12.133090 | 1992.934000 | 0.076752 | 7.29477 | 100.00 |
| 12.750880 | 243.314400 | 0.076752 | 6.94270 | 12.21 |
| 14.404470 | 228.384400 | 0.076752 | 6.14920 | 11.46 |
| 15.471420 | 182.503800 | 0.076752 | 5.72745 | 9.16 |
| 16.279490 | 128.768800 | 0.102336 | 5.44493 | 6.46 |
| 17.199970 | 1366.306000 | 0.076752 | 5.15556 | 68.56 |
| 17.818710 | 121.344500 | 0.076752 | 4.97791 | 6.09 |
| 18.228380 | 1990.086000 | 0.102336 | 4.86695 | 99.86 |
| 18.481630 | 1146.784000 | 0.102336 | 4.80082 | 57.54 |
| 18.999820 | 928.888800 | 0.076752 | 4.67104 | 46.61 |

TABLE 3-continued

X-ray powder diffraction results of Utidelone semihydrate

| Pos. [°2Th.] | Height [cts] | FWHM Left [°2Th.] | d-spacing [Å] | Rel. Int. [%] |
|---|---|---|---|---|
| 20.109480 | 222.418000 | 0.102336 | 4.41572 | 11.16 |
| 20.351990 | 669.859400 | 0.102336 | 4.36365 | 33.61 |
| 21.242110 | 848.766600 | 0.102336 | 4.18277 | 42.59 |
| 21.673660 | 220.805600 | 0.102336 | 4.10045 | 11.08 |
| 23.488450 | 448.113400 | 0.102336 | 3.78759 | 22.49 |
| 24.375570 | 863.059600 | 0.102336 | 3.65172 | 43.31 |
| 24.785660 | 52.506960 | 0.076752 | 3.59222 | 2.63 |
| 25.591940 | 593.566200 | 0.102336 | 3.48084 | 29.78 |
| 26.124380 | 629.429400 | 0.102336 | 3.41110 | 31.58 |
| 27.379300 | 43.102740 | 0.307008 | 3.25754 | 2.16 |
| 28.279930 | 71.329510 | 0.127920 | 3.15581 | 3.58 |
| 29.084560 | 129.744900 | 0.204672 | 3.07031 | 6.51 |
| 30.518850 | 38.762480 | 0.511680 | 2.92920 | 1.94 |
| 33.350070 | 159.679800 | 0.153504 | 2.68672 | 8.01 |
| 34.857010 | 55.001420 | 0.153504 | 2.57395 | 2.76 |
| 36.455820 | 31.499730 | 0.255840 | 2.46465 | 1.58 |
| 37.080260 | 98.544650 | 0.076752 | 2.42457 | 4.94 |

The X-ray diffraction pattern is shown in FIG. 1.

Example 2

After dissolving 7.5 g of dry Utidelone in 100% ethanol at a concentration of 20 mL/g, sterile filtration was performed using a 0.2 urn membrane, and the filtrate was slowly added with 40 water while stirring, then adding a small amount of seed crystals, and continuing to stir for 30 minutes. The rest of the water was then added to the solution to a 50% ethanol concentration. During the stirring process, the temperature of the solution was brought to 4° C. by using a cooling water bath, and the stirring was continued for 2-12 hours. The crystals were vacuum filtered, then quickly washed with a cooled 30% aqueous ethanol solution at 4° C., and then dried in a vacuum oven for 48 hours. 6 g of product was obtained. The X-ray diffraction pattern of the product is shown in FIG. 2, and its main characteristic peaks appear at reflection angle 20 of about 12.4, 17.5, 20.4, 21.6, 23.8, 24.8, 25.8, 33.9, which is different from the semihydrate crystal.

Example 3

Utidelone Semihydrate Crystal was Determined to be Stable at High Temperature

Stability test: The stability test of the semihydrate crystal was carried out under the following conditions:

Storage condition 1: 2-25° C., stored in a sealed state for more than 3 years, confirmed by NMR, HPLC, X-ray powder diffraction and infrared spectrum analysis, etc., the semihydrate crystal was stable (no changes in content, no impurities due to degradation, no changes in appearance and physicochemical properties).

Storage Condition 2: 25° C., 60%±10% RH, unsealed storage for more than 3 days, after the sample was continued to be stored at 25° C. for 1 year, it was confirmed by NMR, HPLC, X-ray powder diffraction and infrared spectrum analysis, etc., the semihydrate crystal was stable (no changes in content, no impurities due to degradation, no changes in appearance and physicochemical properties).

Storage condition 3: Stored in a sealed state at 40° C. for more than 2 years. It was confirmed by NMR, HPLC, X-ray powder diffraction and infrared spectrum analysis, etc., the semihydrate crystal was stable (no changes in content, no impurities due to degradation, no changes in appearance and physicochemical properties).

Storage Condition 4: Stored at 60° C. for more than 1 year. It was confirmed by NMR, HPLC, X-ray powder diffraction and infrared spectrum analysis, etc., the semihydrate crystal was stable (no changes in content, no impurities due to degradation, no changes in appearance and physicochemical properties).

Example 4

Utidelone Semihydrate Crystal is Stable Under High Humidity and Strong Light

The semihydrate crystal obtained in Example 1 was placed under the condition of relative humidity of 90%±5% for 10 days, and samples were taken on the 5th and 10th days. The samples were stable: no obvious changes in content, no impurities due to degradation, no changes in appearance and physicochemical properties, and the moisture content was basically unchanged.

Utidelone anhydrous crystal was placed under the condition of relative humidity of 90±5% for 10 days. Samples were taken on the 5th and 10th days. The moisture content increased and the moisture absorption was obvious.

The semihydrate crystal obtained in Example 1 was placed in a light box, and placed for 10 days under the condition that the light intensity was 4500 lx±500 lx. The crystal was stable: no obvious changes in content, no impurities due to degradation, no changes in appearance and physicochemical properties, and the moisture content was basically unchanged.

Example 5

Utidelone Semihydrate Crystal Showed Good Solubility in a Solubility Test

The semihydrate crystal obtained in Example 1 was placed in a 0.1N hydrochloric acid solution, and the crystal was stable: no obvious degradation impurities were produced. Solubility >5 mg/ml.

| Solvent | Solubility |
|---|---|
| Ethanol | >50 mg/ml |
| Methanol | >50 mg/ml |
| Propylene Glycol | >50 mg/ml |
| DMSO | >50 mg/ml |
| Benzyl alcohol | >50 mg/ml |
| 50% Ethanol, 30% Propylene Glycol, 20% Castor Oil | >100 mg/ml |

About 25 mg of the semihydrate crystal obtained in Example 1 was formed self-emulsifying solution in 10% ethanol, 5% propylene glycol, 45% castor oil, and 40% corn oil. The self-emulsifying solution has good stability and no obvious degradation impurities were observed. It was able to be completely dissolved in 100 ml of water, showing good solubility and no solid was precipitated within 1 hour.

Example 6

PK Study on Intravenous Administration of the Pharmaceutical Composition Containing Utidelone Semihydrate Crystal This example fully illustrates that the composition may be used to prepare a medicament for treating solid tumors such as breast cancer, intestinal cancer, liver cancer, stomach cancer, lung cancer, etc., and its curative effect is excellent.

Utidelone injection was prepared with Utidelone crystals (crystal A or mixed crystals containing crystal A) and 50% v/v absolute ethanol (USP), 30% v/v propylene glycol (USP) and 20% v/v polyoxyl castor oil 1 (Cremophor EL or ELP) as a solubilizer. The injection has low water content and high stability.

Subjects were given intravenous infusion of Utidelone 40 mg/m2, once a day, for 5 consecutive days, the elimination half-life t½ of Utidelone in plasma after administration on the 1st and 5th days were respectively 8.6±0.1 h and 8.2±1.1 h, MRT were respectively 4.5±0.8 h and 5.1±0.7 h, AUC (0-24) were respectively 4178.3±1008.5 h·ng/mL and 4547.4±1628.1 h·ng/mL; plasma clearance CL were 9.2±2.7 L/h/m2 and 8.9±3.9 L/h/m2, respectively; apparent volume of distribution were 114.0±35.2 L/m2 and 109.1±62.6 L/m2, respectively. The difference between the first time and the last time of all parameters was not statistically significant, indicating that after continuous administration of 40 mg/m2, the drug did not accumulate and induce accelerated metabolism in the body, and thus the metabolic disposal of Utidelone in the body did not change.

The invention claimed is:

1. Utidelone semihydrate crystal (A), which is single crystal, and the asymmetric structure unit is composed of four Utidelone molecules (crystallographically independent 1) and two water molecules to form the semihydrate crystal form.

2. A pharmaceutical composition comprising the crystal according to claim 1 and a pharmaceutically acceptable excipient.

3. The pharmaceutical composition according to claim 2, wherein the B pharmaceutical composition is used for treating a solid tumor in mammal.

4. A method of treating a solid tumor in mammal, comprising administering a therapeutically effective amount of the pharmaceutical composition according to claim 2.

5. The method according to claim 4, wherein the solid tumor is selected from the group consisting of breast cancer, lung cancer, colon cancer, gastrointestinal tumors, gynecological tumors, head and neck squamous cell carcinoma, esophageal cancer, pancreatic cancer, bile duct cancer, skin cancer, brain cancer and liver cancer.

6. A pharmaceutical composition, which is obtained by utilizing the crystal according to claim 1 and a pharmaceutically acceptable excipient.

7. The pharmaceutical composition according to claim 3, wherein the mammal is a human.

8. The method according to claim 5, wherein the gastrointestinal tumor is a stomach cancer and the gynecological tumor is selected from ovarian cancer and cervical cancer.

* * * * *